(12) United States Patent
Zhou et al.

(10) Patent No.: US 8,920,719 B2
(45) Date of Patent: Dec. 30, 2014

(54) IMMUNOCHROMATOGRAPHIC STRIP DISC FOR MULTIPLEXED DETECTION AND DETECTION METHOD USING THE SAME

(75) Inventors: Lei Zhou, Beijing (CN); Zongmin Du, Beijing (CN); Ruifu Yang, Beijing (CN); Huijie Huang, Shandhai (CN)

(73) Assignee: Institute of Microbiology and Epidemiology, Acadamy of Military Medical Sciences, Beijing (CN)

( * ) Notice: Subject to any disclaimer, the term of this patent is extended or adjusted under 35 U.S.C. 154(b) by 898 days.

(21) Appl. No.: 12/530,516

(22) PCT Filed: Apr. 23, 2007

(86) PCT No.: PCT/CN2007/001344
§ 371 (c)(1),
(2), (4) Date: Jan. 11, 2010

(87) PCT Pub. No.: WO2008/110044
PCT Pub. Date: Sep. 18, 2008

(65) Prior Publication Data
US 2010/0120173 A1    May 13, 2010

(30) Foreign Application Priority Data
Mar. 9, 2007    (CN) .......................... 2007 1 0064311

(51) Int. Cl.
*G01N 33/48* (2006.01)
*G01N 33/558* (2006.01)
*B01L 3/00* (2006.01)
*G01N 30/92* (2006.01)

(52) U.S. Cl.
CPC ....... *G01N 33/558* (2013.01); *B01L 2300/0816* (2013.01); *B01L 2300/0819* (2013.01); *B01L 2300/0867* (2013.01); *G01N 30/92* (2013.01); *B01L 3/5023* (2013.01); *B01L 3/5025* (2013.01); *B01L 2300/0654* (2013.01); *B01L 2300/0825* (2013.01); *B01L 2300/0864* (2013.01)

USPC .............. 422/64; 422/68.1; 422/70; 422/420; 422/506; 422/507; 435/288.6; 435/305.2

(58) Field of Classification Search
USPC ........... 422/68.1, 70, 82.05, 64, 72, 420, 506, 422/507; 435/288.6, 305.2
See application file for complete search history.

(56) References Cited

U.S. PATENT DOCUMENTS 6,203,757 B1 *  3/2001  Lu et al. ........................ 422/412
6,514,769 B2    2/2003  Lee
(Continued)

FOREIGN PATENT DOCUMENTS

| AU | 2007349145 | 5/2012 |
|---|---|---|
| CN | 101261270 | 11/2012 |
| JP | 4851597 | 1/2012 |

OTHER PUBLICATIONS

International Search Report for PCT/CN2007/001344 dated Dec. 20, 2007.

*Primary Examiner* — Lyle Alexander
(74) *Attorney, Agent, or Firm* — Amin, Turocy & Watson, LLP

(57) ABSTRACT

Provided is a strip-assembled immunochromatographic disc, containing: a base, a lid engaged with the base and a draining piece disposed between the strips on the base and the lid, wherein a sampling opening is disposed on the lid directly facing to the draining piece, and the said sampling opening intercommunicates to a draining groove provided on the inner side of the lid which is formed by a plurality of draining channels; several strip stages are provided on the base with their location and number corresponding to those of the draining channels provided on the lid, and the edge of the draining piece laps to the sample pads of the strips carried on the stage adjacent to one end of the sampling opening. Also provided is a method of performing multiplexed immnochromatographic detection using the strip disc to accomplish the detection of multiple target analytes in one sample in an assay.

14 Claims, 10 Drawing Sheets

(56) References Cited

U.S. PATENT DOCUMENTS 6,573,108 B1 6/2003 Hardman et al.
6,740,293 B1 5/2004 Deng
2004/0152206 A1 8/2004 Davis et al.
2005/0227370 A1 10/2005 Ramel et al.
2006/0008847 A1 1/2006 Ramel et al.
2009/0061507 A1* 3/2009 Ho .............................. 435/288.6

* cited by examiner

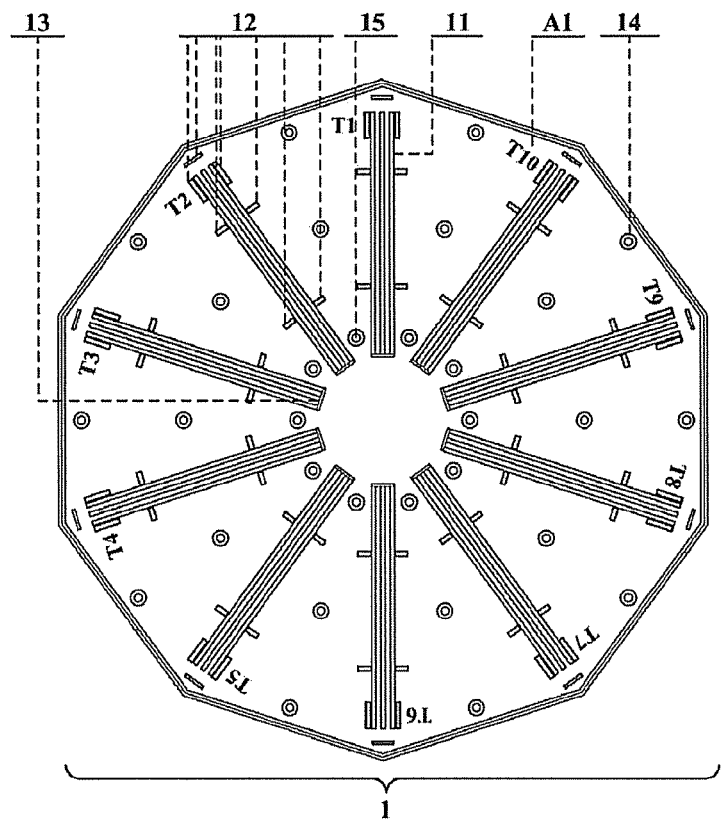
Figure 6
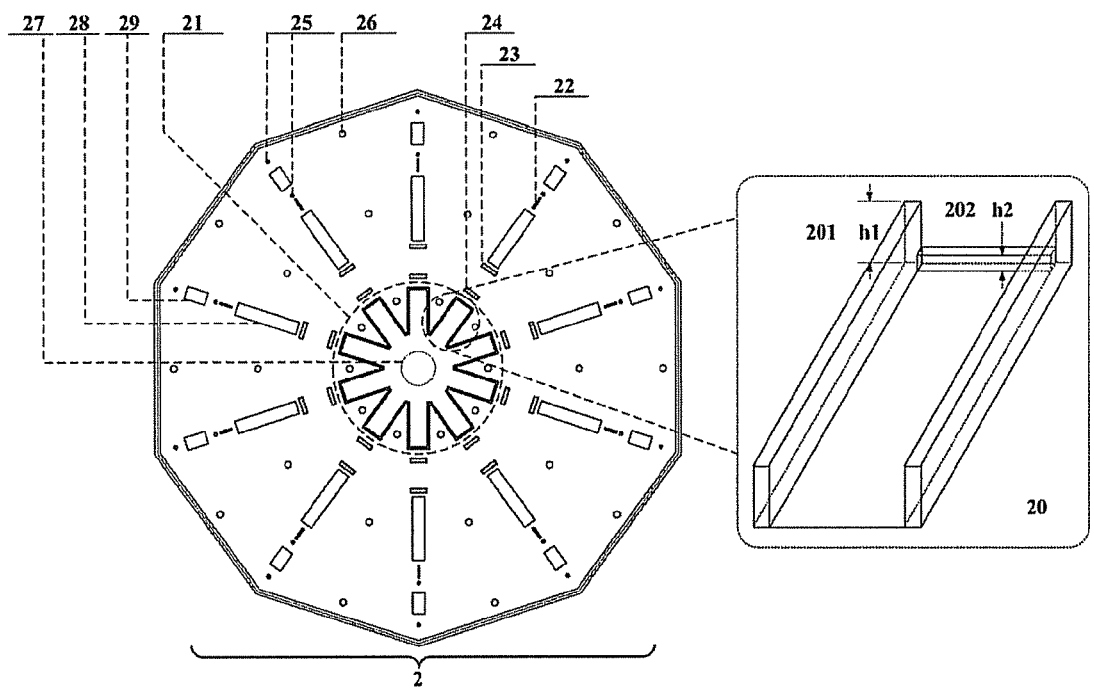
Figure 7A
Figure 7B

IMMUNOCHROMATOGRAPHIC STRIP DISC FOR MULTIPLEXED DETECTION AND DETECTION METHOD USING THE SAME

TECHNICAL FIELD

The present invention belongs to the field of immunologic diagnosis, and relates to a multiplexed immunochromatographic detection technique. The present invention provides an immunochromatographic strip disc and a method of multiplexed immunochromatographic detection that simultaneously analyzes various analytes in one sample by using the disc.

BACKGROUND

Immunochromatography is a kind of mature technique for on-site rapid detecting. A conventional immunochromatographic strip 4 is shown in FIG. 1, and contains the following components: an analytical membrane (mainly nitrocellulose membrane) 101, a conjugate pad (mainly glass fiber) 102, a sample pad 103 (mainly glass fiber or absorbent paper) and an absorbent pad (mainly absorbent paper) 104. The above components are fixed on the sticky substrate 105 with proper overlapping sequence. The overlapping of the above components ensures the continuity of liquid flow on the strip. When performing the detection, the sample is added to the sample pad 103. The sample enters the conjugate pad 102 through penetration and siphon actions to redissolve the marker-biomolecular conjugates therein. Under the siphon effect of absorbent pad 104, the sample and conjugates leave the conjugate pad 102, enter into the membrane 101 and flow toward the absorbent pad 104 inside the membrane 101. During the process, a specific immunologic reaction occurs between conjugates, target analytes, test band 106 and quality control band 107 to generate indicative signals. Markers which are commonly used to generate indicative signals include colloid gold, fluorescein, dye, etc. However, every kind of immunochromatographic strip has to follow the detecting mode of one-to-one, namely, only one analyte can be detected in one assay for one sample. This kind of detecting mode is complex and time-consuming when used for the screening of a variety of target analytes in suspected samples.

SUMMARY

One purpose of the invention is to provide an immnochromatographic strip disc used for multiplexed detection which is simple and time-saving compared with one-to-one detecting mode in the prior art.

Another purpose of the invention is to provide a method of performing multiplexed detection using the immnochromatographic strip disc of the present invention. Thus, a detecting mode of one-to-many is implemented, namely, variety of target analytes can be simultaneously detected in one assay for one sample.

The disc of the present invention comprises: a base, a lid engaged with the base, a draining piece disposed between a strip on the base and the lid. There is a sampling opening on the lid which directly faces the draining piece. The sampling opening intercommunicates to a draining groove provided on the inner side of the lid, which is formed by a plurality of draining channels. There are several strip stages provided on the base with their location and number corresponding to those of the draining channels provided on the inner side of the lid. The edge of the draining piece laps to a sample pad of the strips carried on the stage adjacent to one end of the sampling opening.

The above said immunochromatographic disc may have one of the following shapes including a circle, a square, a rectangle, a diamond, a regular polygon. The sampling opening is provided in the geometric center of one of the above shapes. Several strip stages of the base are arranged in central symmetry or axial symmetry.

Several sets of fixing stoppers are disposed along the edge of every stage in the immunochromatographic disc. Numbering regions are provided on each of the stage near the edge of the base of the disc.

The strip stage comprises three protuberances. The end adjacent to the symmetric center or axis is sealed by equal-height stoppers.

Several sets of pressing pieces are disposed at interval on the inner side of the lid at the position where the channel of the draining groove extends outwards, and a result observing window, an endpoint indicating window, and fixing rivets are also sequentially disposed on inner side of the lid.

Several rows of excavate rivets are disposed on the base of the disc, which correspond to the salient rivets on the inner side of the lid.

The draining channel comprises two upper fringes and a lower fringe, and all the draining channels connect sequentially. The inner side of the two upper fringes are occluded with the edge of the stage and extend directly to the under side of the base. The relationship between the height of the lower fringe (h2) and the height of the upper fringe (h1) is expressed as follows:

$$h2 = h1 - (\text{the height of the stage} + \text{the thickness of the sticky substrate of the strip} + \text{the thickness of the sample pad of the strip}).$$

Specifically, if the imnnochromatographic strip disc has one of the shapes including a circle, a diamond and a regular polygon, the sampling opening is disposed at the geometric center and several strip stages on the base can be arranged in central symmetry.

In other words, if the above said disc has one of the shapes including a square and a rectangle, the sampling opening can be disposed at the symmetric axis and several strip stages on the base can be arranged in axial symmetry.

The numbers on the outer side of the lid correspond to those on the base of the disc. In addition, the ID window used for marking the serial number of the assayed sample, holding indication for users and the indication for inserting direction are also disposed.

The multiplexed detection method provided by the invention can be used for qualitative detection, comprising the following acts:

Act 1: Assembly the immunochromatographic disc by placing different types of the strips on the corresponding stage with different numbers.

Act 2: Adding a liquid sample through the sampling opening and judge the test endpoint through the endpoint indicating window.

Act 3: Observe and record the results of the different strips through the result observing windows.

Act 4: Compare the test results with the standard so as to judge the occurrence of a certain kind of immunologic reaction and determine the existence of certain kinds of analytes.

The multiplexed detection method provided by the invention can be used for quantitative detection, comprising the following acts:

Act 1: Assembly the immunochromatographic disc by placing different types of strips on the corresponding stage with different numbers.

Act 2: Adding a liquid sample through the sampling opening and judge the test endpoint through the endpoint indicating window.

Act 3: According to the holding indication for users and the indication for inserting direction outside the lid, insert the disc into the detecting apparatus.

Act 4: Power on the detecting apparatus to analyze one strip quantitatively through the result observing window. The test result corresponding to this strip is displayed on the apparatus.

Act 5: Rotate or move the disc to the next numbered strip and power on the apparatus again to perform another quantitative analysis.

Act 6: Repeat the act 5 until all strips on the disc are analyzed.

Act 7: Determine the existence of a certain kind of analytes and its concentration.

one of the core ideas of the invention lies in establishing a detecting mode for multiplexed immunochromatographic detection through a unique design of the immunochromatographic disc so that immunochromatographic reaction can occur simultaneously and synchronously in multiple strips to implement the multiplexed detection of one sample.

The invention has the following technique advantages:

Compared with the one-to-one detecting mode in the prior art, the invention establishes a new detecting mode for multiplexed immunochromatographic detection by designing the immunochromatographic strip disc so that the existence of various target analytes can be determined in one assay for one sample. Thus, a detection mode of one-to-many is achieved. In the prior art, although the mode of performing multiplexed detection with several kinds of the strips was mentioned briefly, it does not ultimately resolve the problems that exist necessarily during the multiplexed immunochromatography detection, such as uneven distribution of the liquid sample, non-uniform immunochromatography reaction and liquid sample loss caused by overflow etc. so that the multiplexed immunochromatography-based detection can not be actually achieved. The present invention directly resolves the above problems by means of the special arrangement of the strips, the usage of the draining piece and the design of the draining groove on the lid of the disc. With these advantages, the synchronous immunochromatography-based detection can be carried out smoothly to be uniform and prompt.

BRIEF DESCRIPTION OF THE DRAWINGS

FIG. 6: a graph showing the base of the centrally symmetric 10 strips-assembled disc.

FIG. 7A: a graph showing the inner side of the centrally symmetric 10 strips-assembled disc.

FIG. 7B: a graph showing the structure of the draining channel on the inner side of the centrally symmetric 10 strips-assembled disc.

THE DETAILED DESCRIPTION

Figure 1:
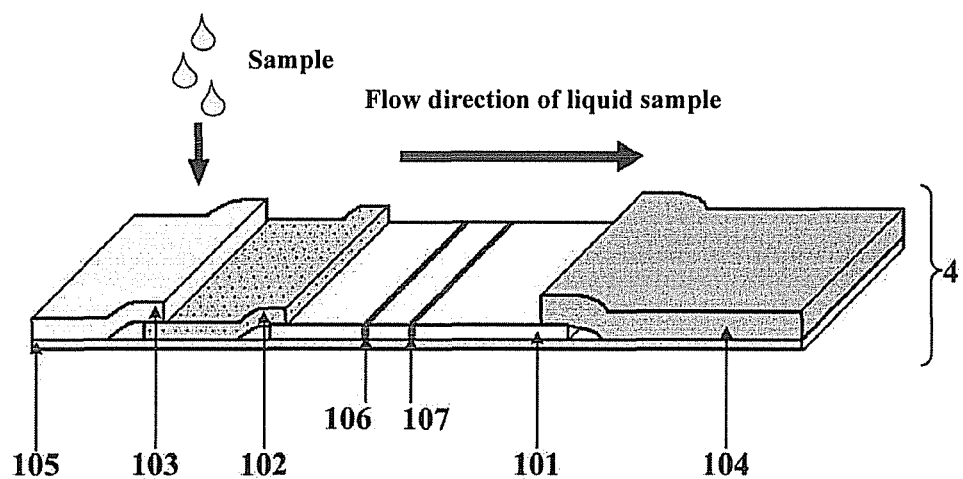
FIG. 1: a graph showing the structure of the strip.
Figure 8:
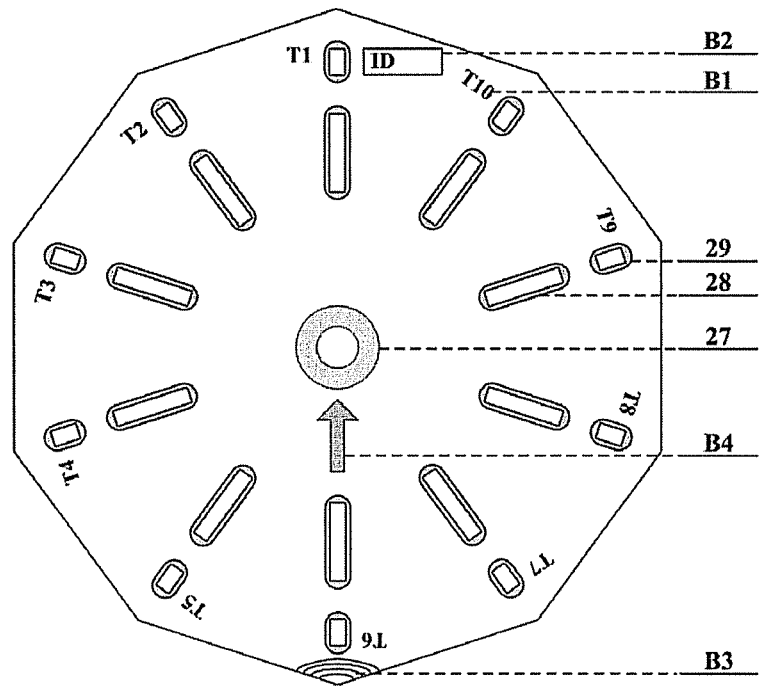
FIG. 8: a graph showing the outer side of the centrally symmetric 10 strips-assembled disc.
Figures 11A, 11B:
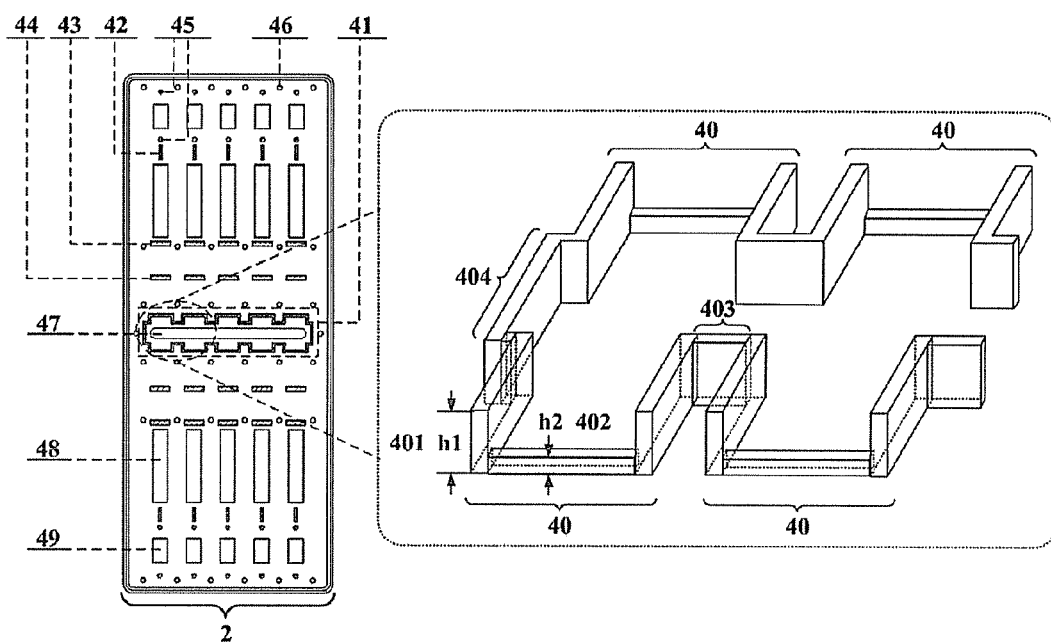
FIG. 11A: a graph showing the inner side of the lid of the axially symmetric 10 strips-assembled disc.
FIG. 11B: a graph showing the structure of the draining channel on the inner side of the lid of the axially symmetric 10 strips-assembled disc.
Figure 12:
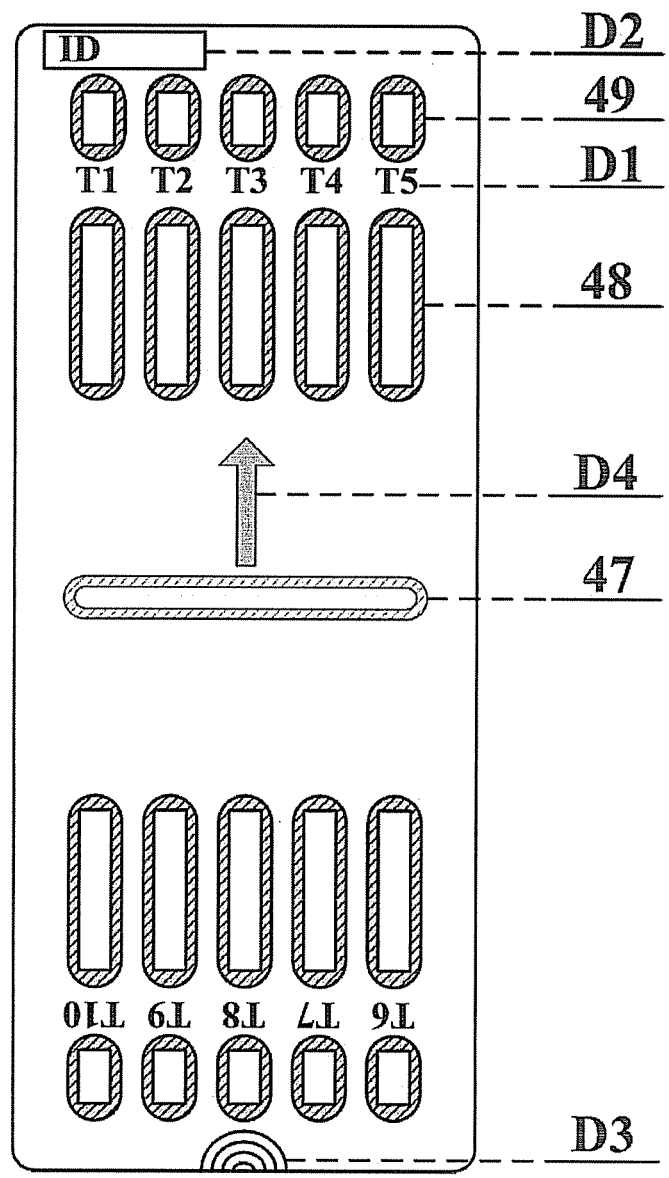
FIG. 12: a graph showing the outer side of the lid of the axially symmetric 10 strips-assembled disc.

The immunochromatographic strip disc of the present invention comprises four components: a base 1 (see FIG. 2, FIG. 6, FIG. 10), a lid 2 (see FIG. 3A/3B and FIG. 4, FIG. 7A/7B and FIG. 8, FIG. 11A/11B and FIG. 12), draining pieces 3 (see FIG. 5, FIG. 9, FIG. 13) and strips 4 (see FIG. 1). The said base 1 and lid 2 are fitted to engage for use. The said draining piece 3 is disposed between the lid 2 and the strips carried on the base 1.

Figure 10:
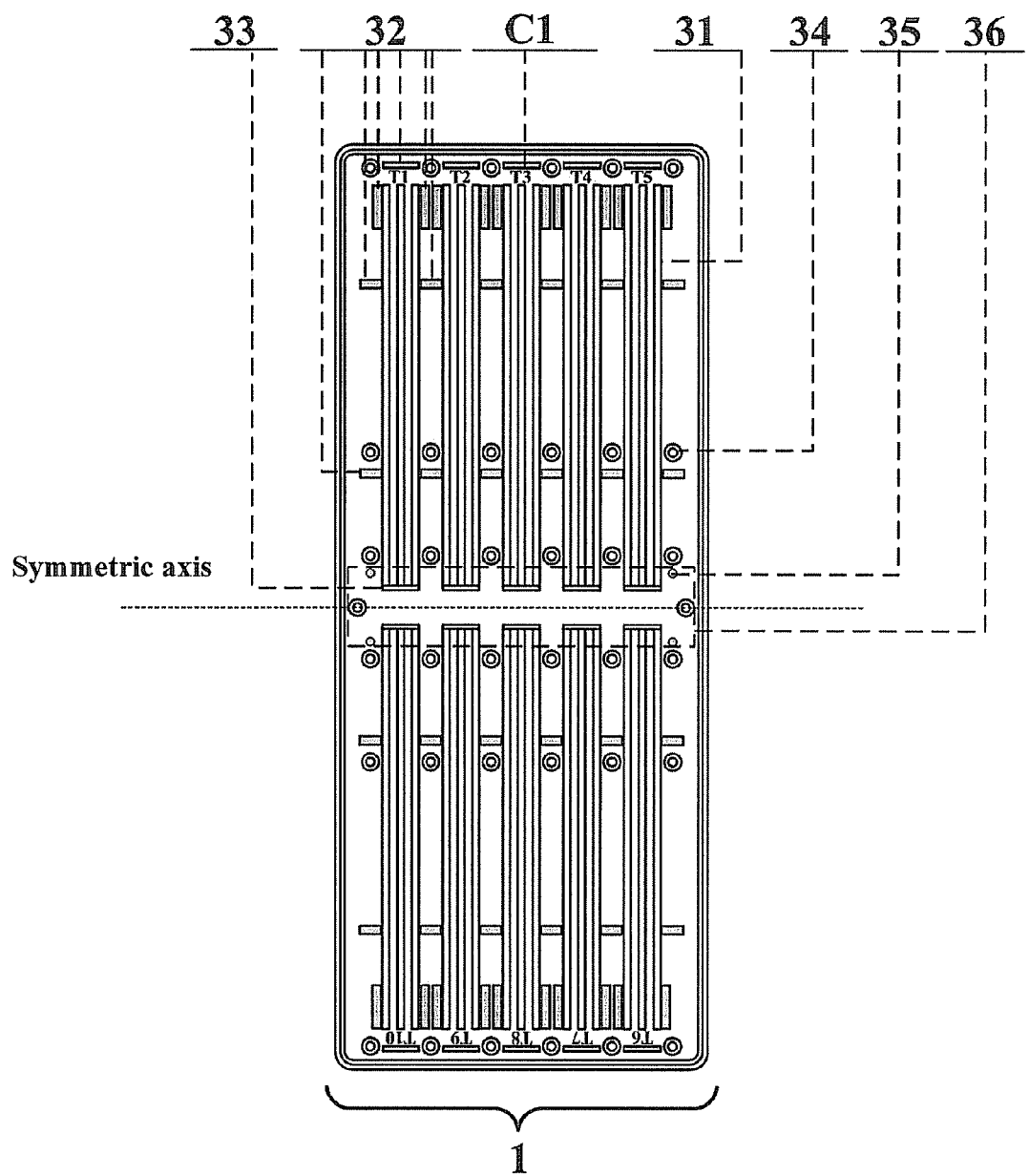
FIG. 10: a graph showing the base of the axially symmetric 10 strips-assembled disc.

The base 1 contains several strip stages 11 which are arranged in central symmetry (see FIG. 2, FIG. 6) or axial symmetry (see FIG. 10). Several sets of fixing stoppers 12 and equal-height stoppers 13 are disposed along the edge of every stage 11. Numbering region A1 is provided on each stage near the edge of the base 1. Several rows of excavate rivets 14 are disposed on the base of the disc.

Figure 2:
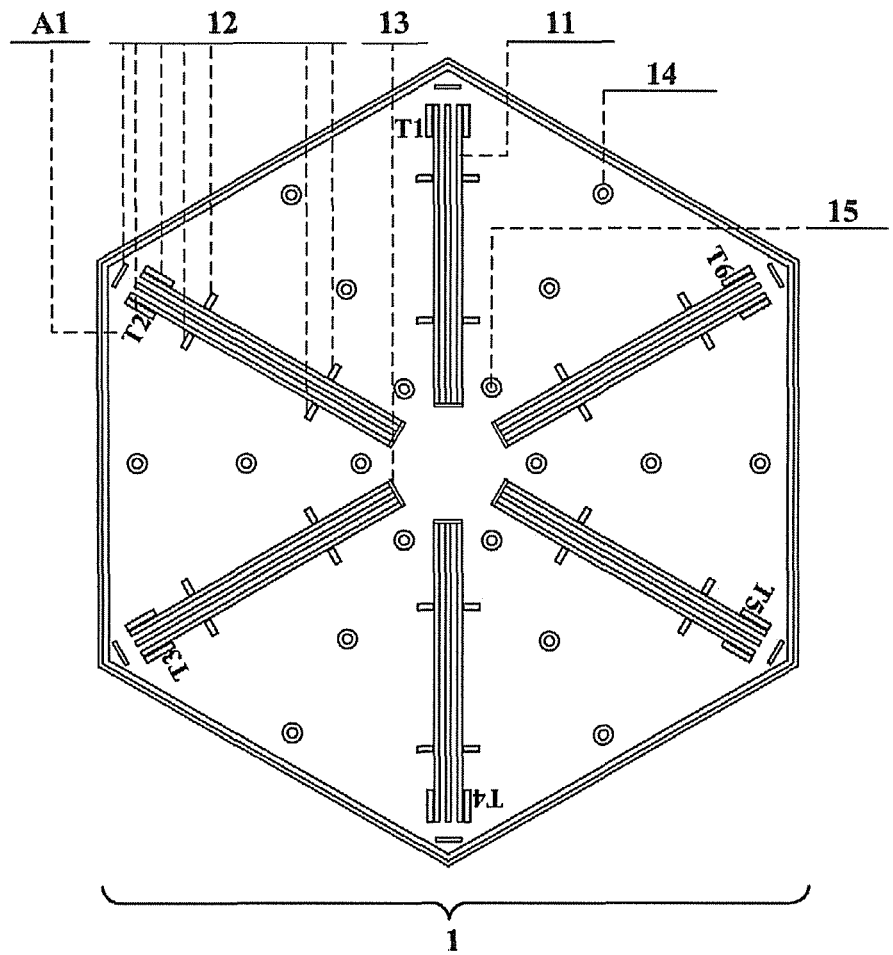
FIG. 2: a graph showing the base of the disc.

As shown in FIG. 2, the said strip stage 11 comprises three protuberances, and the end adjacent to the symmetric center or axis is sealed by equal-height stopper 13 to prevent overflow of the liquid sample. The said fixing stopper 12 is configured around the strip stage 11. The said strip stage 11 is combined with the fixing stoppers 12 for carrying and fixing strips, thereby keeping them in central symmetry or axial symmetry as consistent with strip stages 11, with sample pads of strips gathering at the symmetric center or axis. The said numbering region A1 is provided on the edge of each strip stage 11 for indicating the different types of strips carried on the strip stage 11. The said several rows of excavate rivets 14 are used to engage with the lid 2, wherein the group of excavate rivets 14 adjacent to the symmetric center or symmetry axis innermost can also be used as fixed pins 15 for fixing the draining piece 3.

Figures 3A, 3B:
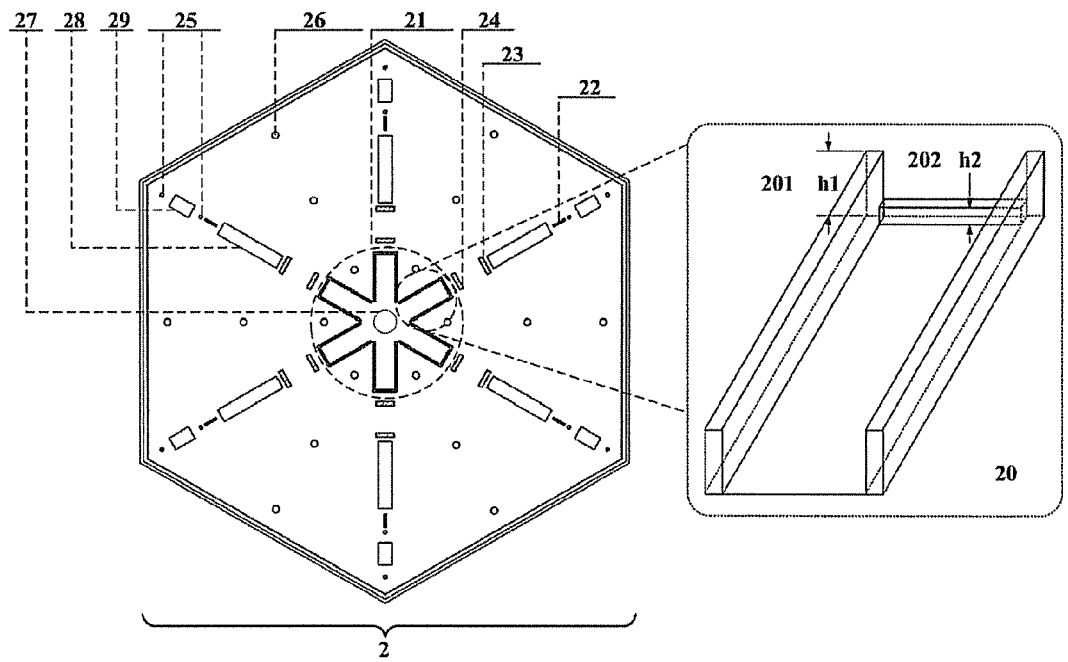
FIG. 3A: a graph showing the inner side of the lid of the disc.
FIG. 3B: a graph showing the structure of the draining channel on the inner side of the lid of the disc.
Figure 4:
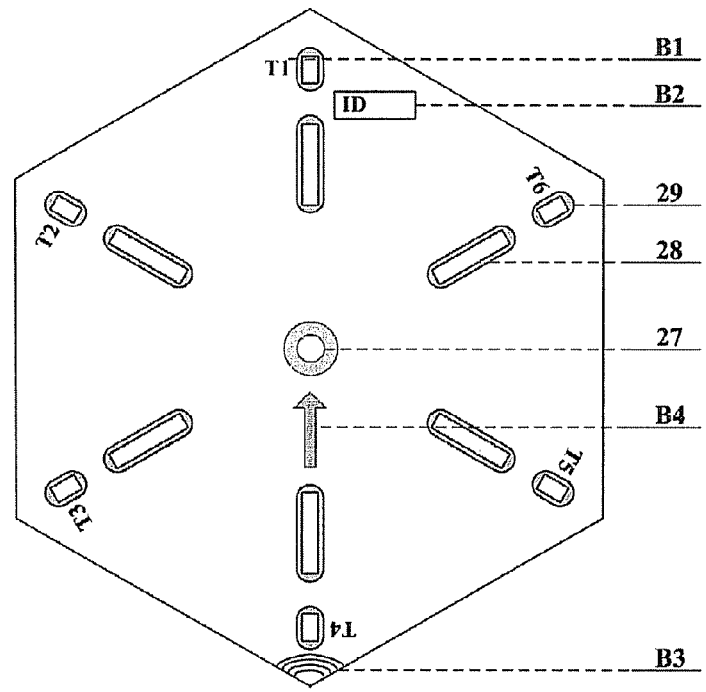
FIG. 4: a graph showing the outer side of the lid of the disc.

Referring to FIG. 3 and FIG. 4, the lid 2 comprises both the inner side and the outer side and consists of the following components: draining groove 21, several sets of pressing pieces 22, 23, 24, fixing rivets 25, several rows of salient rivets 26, sampling opening 27, result observing window 28, endpoint indicating window 29, numerical code B1, ID window B2, holding indication B3 and indication for inserting direction B4. The draining groove 21, pressing piece 22, 23, 24, fixing rivet 25, salient rivets 26 are disposed on the inner side of the lid. The sampling opening 26, the result observing window 27 and the endpoint indicating window 28 penetrate through the inner and outer side of the lid 2. The numerical code B1, ID window B2, the holding indication B3 and the indication for inserting direction B4 are only disposed on the outer side of the lid.

The said draining groove 21 is formed by integrating the draining channels 20 corresponding to each strip. As shown in FIG. 3B, the said draining channel 20 comprises two upper fringes 201 and one lower fringe 202. The inner sides of the said upper fringe 201 occlude with the edge of the stage 11 and extend directly to the underside of the base 1. The relationship between the height h2 of the said lower fringe 202 and the height of the upper fringe h1 is expressed as follows: h2=h1−(the height of the stage+the thickness of the sticky substrate of the strip+the thickness of the sample pad of the strip). The lower fringe 202 chucks the sample pad 103 tightly. The said upper fringes 201 and lower fringes 202, together with the stage 11, equal-height stoppers 13, the strips 4, the draining piece 3, the underside of the base 1 and the inner side of the lid of disc 2, define a closed sample pool and the draining channels corresponding to each strip.

The said three pressing pieces 22, 23, 24 correspond to the overlapping areas of the absorbent pad 104 and the analytic membrane 101, the conjugate pad 102 and the analytic membrane 101, as well as the sample pad 103 and the conjugate pad 102 (see FIG. 1) in turn, which ensures the continuity of the liquid flow in the strip. The said fixing rivet 25 can penetrate into the absorbent pad 104 of the strip for further stabilizing the strip to prevent it from moving. The said salient rivets 26 can interlock with the excavate rivets 14 on the base 1, which further engage and fix the lid 2 and base 1. The said sampling opening 27 is disposed at the center of the lid 2 and corresponds to the draining piece 3 after the base and lid are engaged together. In the process of the detection, the liquid sample is added to the draining piece 3 through the sampling opening 27. The said result observing window 28 and the endpoint indicating window 29 are arranged in line and are disposed corresponding to the stage 11 of the base 1, wherein the result observing window 28 is disposed at the middle of the line and corresponds to the analytic membrane 101 of the strip after the base and lid are engaged together. After the assay is completed, the result can be evaluated from the analytic membrane 101 through the result observing window 28. The endpoint indicating window 29 is disposed on the portion of the line adjacent to the edge of the lid 2 and corresponds to the absorbent pad 104 of the strip after the base and lid are engaged together. The process of the immunochromatography can be monitored through the endpoint indicating window during the detection.

The said numerical code B1 on the lid used for indicating different types of the strip corresponds to the numerical code A1 on the base 1 one to one. The said ID window B2 can be used for marking the serial number of the detected sample. The said holding indication B3 and the indication for inserting direction B4 can indicate the direction for inserting the disc into the apparatus in quantitative detection.

Figure 5:
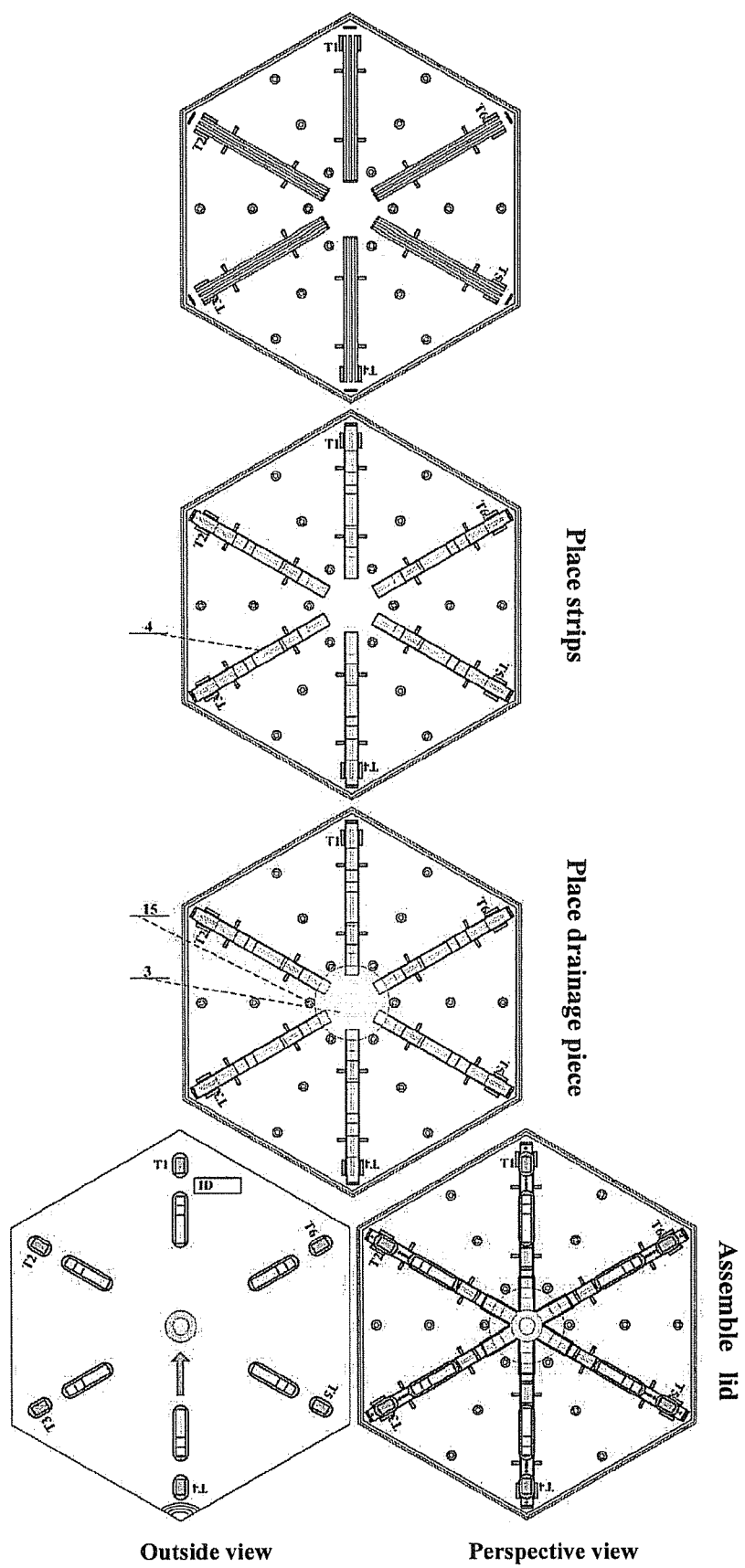
FIG. 5: a graph showing the assembling process of the disc.

As shown in the FIG. 5, the draining piece 3 is a kind of membrane with large bed volume and uniform microscopic structure, which can be of a material such as glassfiber, filter paper, non-woven fabrics, etc. The draining piece 3 is placed in the position corresponding to the draining groove 21 during assembling, which makes it contact the sample pads 103 of each strip and partly overlap the sample pads 103.

The above components are assembled to form the disc of the present invention. The process of assembling is shown in FIG. 5, comprising three acts: placing the strip, placing the draining piece and installing the lid. First, the specific strips are placed on the specific stage 11 according to the numerical code A1 on the base. The arrangement mode of the stages 11 and the positioning action of the fixing stoppers 12 make the strips in central symmetry or axial symmetry with the sample pad gathering. Then, draining piece 3 is placed with excavate rivets 14 on the innermost portion of the base 1 as the fixing rivet 15. The draining piece 3 overlaps with the sample pads of all strips partly. The large bed volume of the draining piece 3 can prevent the overflow of the liquid sample. Meanwhile, the uniform microscopic structure of the draining piece ensures the uniformity of the sample distribution to each strip. In the end, the excavate rivet 14 on the base 1 interlock with the salient rivet 26 on the lid 2 to integrate the strip disc. In the assembled disc, the sampling opening 27, the result observing windows 28 and the endpoint indicating windows 29 of the lid correspond to the draining piece 3 fixed on the base 1, analytic membranes 101 and absorbent pads 104 of each strip, respectively. Furthermore, the three pressing pieces 22, 23, 24 correspond to the overlapping area of the absorbent pad 104 of each strip and the analytic membrane 101, the overlapping area of the conjugate pad 102 and the analytic membrane 101, as well as the overlapping area of the sample pad 103 and the conjugate pad 102, which ensures the continuity of each chromatographic channels. In order to prevent the overflow of the liquid sample and ensure the uniformity of the chromatographic reaction in each strip, the unique draining groove 21 is designed on the inner side of the lid 2, including the draining channels 20 corresponding to each strip. The inner sides of the upper fringes 201 on both sides of the draining channel 20 occlude with the edge of the stage 11 and extend directly to the underside of the base 1. The lower fringe 202 on the middle of the draining channel 20 chunks the sample pad tightly. In addition, the face-center end of the stage 11 is sealed by the equal-height stopper 13. Following the buckling and closing of the base and lid of disc, the stage 11, equal-height stoppers 13, the strips 4, the draining piece 3, the draining groove 21 and the underside of the base 1 and the inner side of the lid 2 define a closed sample pool and draining channels corresponding to each strip, thereby effectively preventing sample loss and at the same time ensuring the synchronism and uniformity of absorption of the sample by each strip.

In summary, the disc of the invention has the following three technical features:
1. The arrangement of strips in central symmetry or axial symmetry ensures the uniformity of absorption of the sample by each strip;
2. The draining piece partly overlapping with the sample pad of each strip has a large bed volume to prevent the overflow of the liquid sample. Meanwhile, the uniform microscopic structure ensure the uniformity of the sample distribution;
3. The draining groove on the inner side of the lid and the base define a closed space for reaction and draining, which ensures the uniformity of the reaction in each strip and prevents the overflow of the liquid sample at the same time.

The above said immunochromatographic strip disc may have one of the shapes including circle, square, rectangle, diamond, regular polygon and any other geometrical shapes. The said disc can carry N strips, wherein N is natural number. Therefore, the disc of the invention may have various modifications. The present invention will be described by way of the specific examples, but is not intended to be limited to the following examples.

The detecting method of the invention can be used for the qualitative detection, comprising the following acts:
1. Assembly the immunochromatographic disc by placing different types of the strips on the stage with different numbers.
2: Adding the liquid sample through the sampling opening and judge the test endpoint through the endpoint indicating window.

3: Observe and record the results of the different strips through the result observing window.
4: Compare the test results with the standard so as to determine the occurrence of a certain kind of immunologic reaction and determine the existence of certain kinds of analytes.

The detecting method of the invention can also be used for the quantitative detection, comprising the following acts:
1: Assembly the immunochromatographic disc by placing different types of the strips on the stage with different numbers.
2: Adding the liquid sample through the sampling opening and judge the test endpoint through the endpoint indicating window.
3: According to holding indication for users and the indication for inserting direction outside the lid, insert the disc into the detecting apparatus.
4: Power on the detecting apparatus to analyze one strip quantitatively through the result observing window. The test result corresponding to this strip is displayed on the apparatus.
5: Rotate or move the disc to the next numbered strip and power on the apparatus again to perform another quantitative analysis.
6: Repeat the act 5 until all strips of the disc are analyzed.
7: Determine the existence of certain kind of analytes and its concentration.

The Example 1

The Centrally Symmetric 6 Strips-Assembled Disc

FIGS. 2-5 show the structure and the assembling process of the central symmetric 6 strips-assembled disc. The disc according to this example has a shape of hexagon with its geometric center as symmetric center, which is designed to carry six strips. All the sample pads 103 of the strips point to the symmetric center. The details for the disc according to this example have been described as discussed above with reference to Figures and its description will be omitted.

The Example 2

The Centrally Symmetric 10 Strips-Assembled Disc

Figure 9:
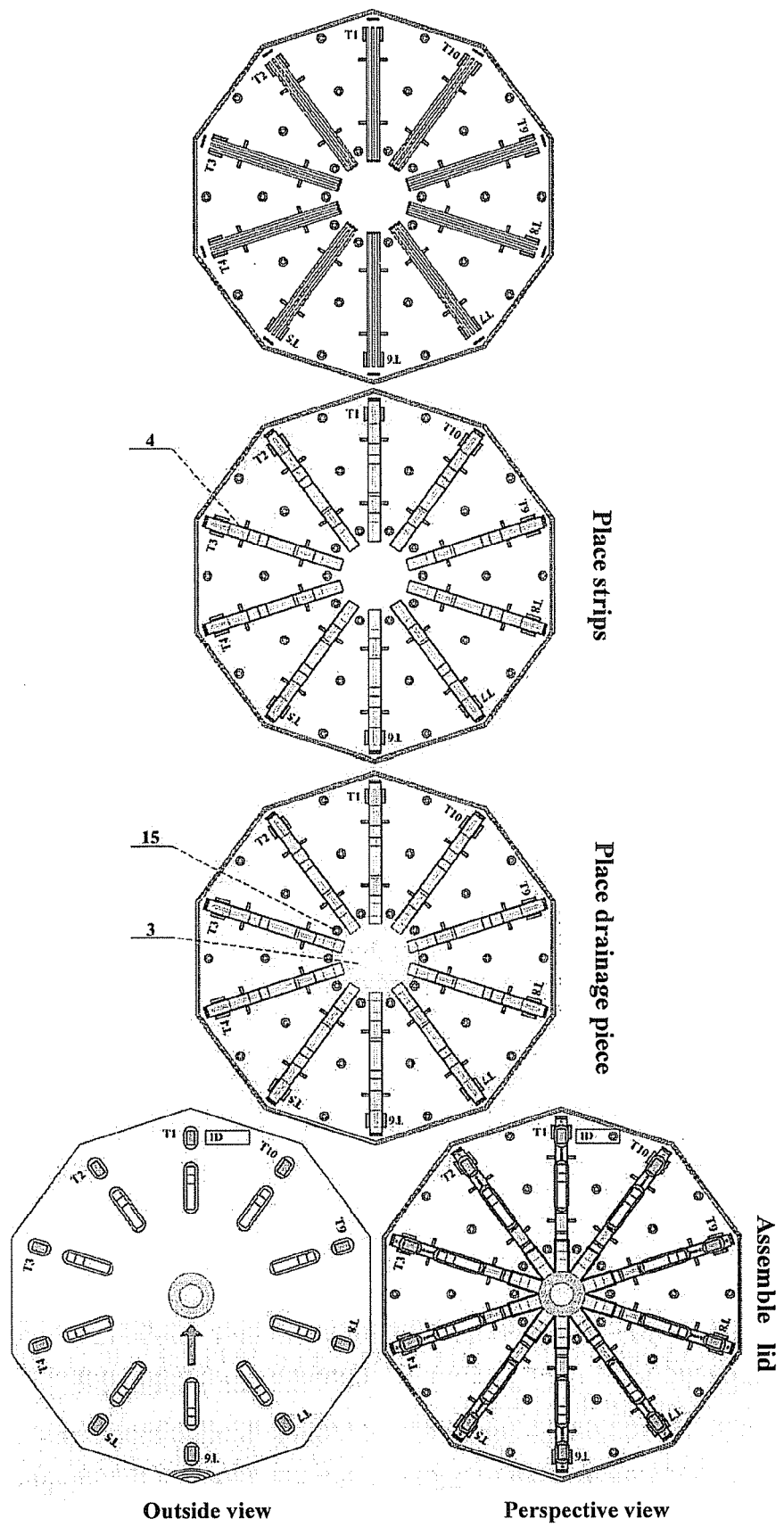
FIG. 9: a graph showing the assembling process of the centrally symmetric 10 strips-assembled disc.

FIGS. 6-9 are referenced based on the above description. The centrally symmetric 10 strips-assembled disc according to this example are comprised of base 1 (FIG. 6), lid 2 (FIGS. 7 and 8), draining piece 3 and strips 4 (FIG. 9). The base 1 includes 10 stages 11, 10 sets of fixing stoppers 12, 10 equal-height stoppers 13, 10 sets of pressing pieces 22, 23, 24, and 10 rows of the excavate rivets 14, 10 numerical codes A1. The lid 2 include draining groove 21 consisting of 10 draining channels 20, 10 sets of the pressing pieces 22, 23, 24, 10 sets of fixing rivets 25, 10 rows of salient rivets 26, sampling opening 27, 10 result observing windows 28, 10 endpoint indicating windows 29, 10 numerical codes B1, ID window B2, holding indication B3 and indication for inserting direction B4.

The assembling process (FIG. 9) comprises the following acts: placing the strips 4, placing the draining piece 3 and installing the lid 2. The assembled disc can achieve the uniform reaction of 10 kinds of immunochromatography strips through some special designs. The stages 11 are arranged in central symmetry, and fit with the fixing stoppers 12 and the fixing rivets 25 on the lid to make 10 strips arranging in central symmetry with the sample pads 103 gathering toward the center. Therefore, with such spatial structure, the uniform immunochromatographic reaction on the various strips 4 can be achieved. The excavate rivets 14 on innermost portion of the base 1 fit with the salient rivets 26 on the lid to engage the disc, and can also be used as fixing rivets 15 to fix the draining piece 3 and make it partly overlap with the sample pad 103 of each strip 4. Consequently, with large bed volume and uniform internal structure, the draining piece 3 prevent the overflow of the liquid sample and ensure the even distribution of the sample to each strip, resulting in the uniform reaction on the different strips. The base 1 and the lid 2 of the disc engage together to make the pressing pieces 22, 23, 24 on the inner side of the lid 2 press on the overlapping areas of the absorbent pad 104 and the analytic membrane 101, the conjugate pad 102 and the analytic membrane 101, as well as the sample pad 103 and the conjugate pad 102, which ensures the continuity of immunochromatographic reaction inside the strips. The draining groove 21 on the inner side of the lid 2 is formed by integrated ten draining channels 20 corresponding to each strip 4. Each draining channel 20 includes two upper fringes 201 and one lower fringe 202. The inner sides of two upper fringes 201 occlude with the edge of the stage 11 and extend directly to the underside of the base 1. The relationship between the height of the lower fringe h2 and that of the upper fringe h1 is as follows:

$$h2=h1-(\text{the height of the stage}+\text{the thickness of the sticky substrate of the strip}+\text{the thickness of the sample pad of the strip}).$$

The relationship ensures that the upper fringes 201 occlude with the edge of the stage 11 and chuck to the underside of the base 1, and at the same time, the lower fringe 202 chucks to the sample pad 103 tightly. In addition, the face-center end of stage 11 is sealed by the equal-height stopper 13. Therefore, following the engagement of the base and lid of disc, the stage 11, equal-height stoppers 13, the strips 4, the draining piece 3, the draining groove 21 and the underside of the base 1 and the inner side of the lid 2 define a closed sample pool and immunochromatographic channel, which can ensure that the sample can be distributed to each strip uniformly while preventing loss of the sample due to overflow. During the detection by the assembled disc, the liquid sample is dropped to the draining piece 3 through the sampling opening 27 and then the immune-reaction begins. The process of the immunochromatographic reaction can be monitored through the endpoint indicating window 29 corresponding to the absorbent pad 104 during the detection and the final result can be read through the result observing window 28 corresponding to the analytic membrane. For the strips that can be analyzed quantitatively by the apparatus, the holding indication B3 and the indication for inserting direction B4 on the disc can indicate the inserting direction of the disc.

At last, a synchronous and uniform immunochromatographic reaction can occur on 10 kinds of strips by using the centrally symmetric 10 strips-assembled disc and the final results can be shown visually.

The Example 3

The Axially Symmetric 10 Strips-Assembled Disc

Figure 13:
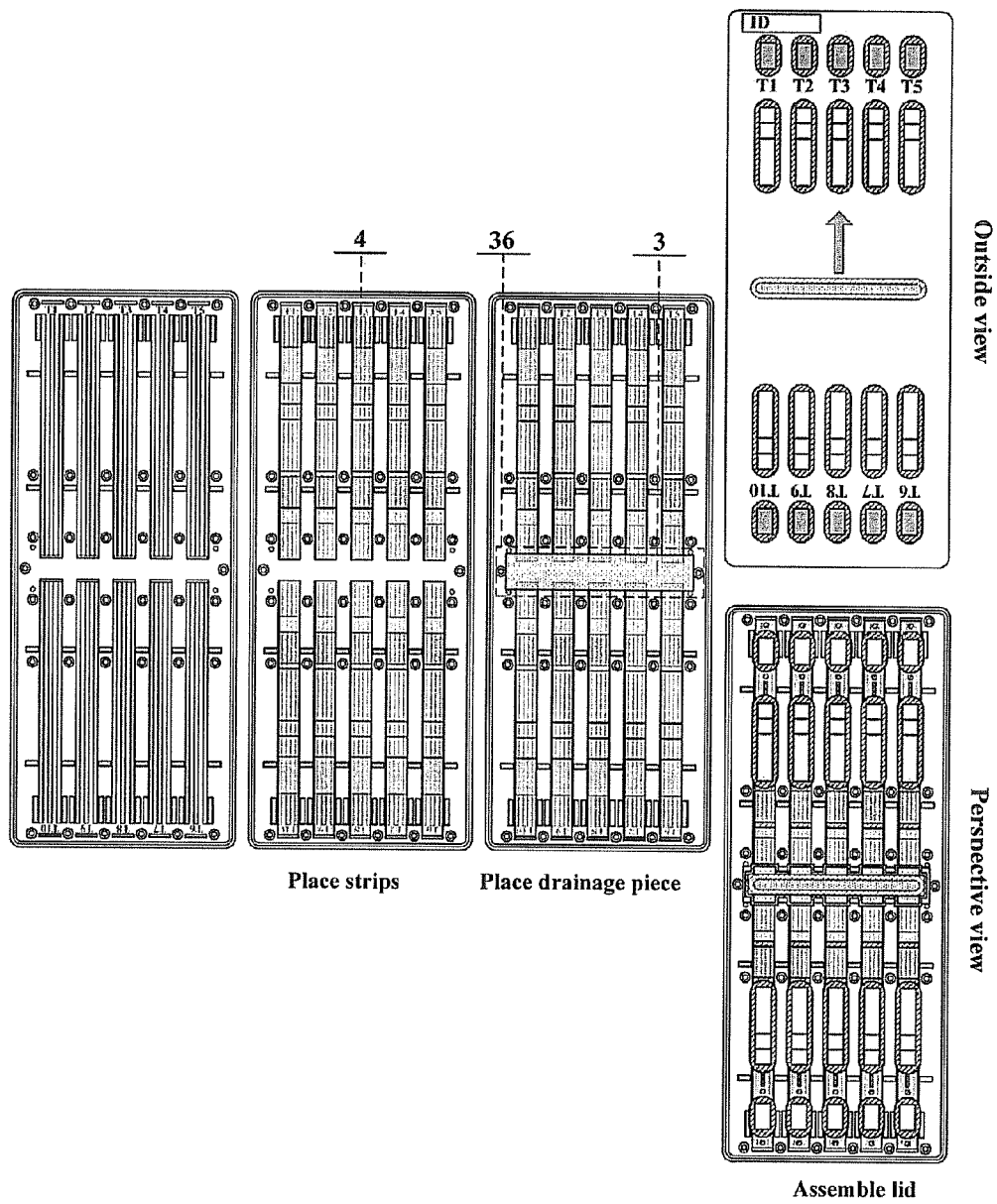
FIG. 13: a graph showing the assembling process of the axially symmetric 10 strips-assembled disc.

FIGS. 10-13 are referenced based on the above description. The axially symmetric 10 strips-assembled disc according to this example has a shape of rectangle, and 10 strips are arranged along the axis symmetrically with 5 strips on each side, which makes sample pads 13 of the strips adjacent to the axis. Specifically, the axially symmetric 10 strips-assembled disc are comprised of base 1 (FIG. 10), lid 2 (FIGS. 11 and 12), draining piece 3 and strips 4 (FIG. 13). The base 1 includes stage 31, fixing stoppers 32, equal-height stoppers 33, excavate rivets 34, salient rivets 35, and numerical codes C1. The lid 2 include draining groove 41, pressing pieces 42, 43, 44, fixing rivets 45, salient rivets 46, sampling opening 47, result observing window 48, endpoint indicating window 49, numerical codes D1, ID window D2, holding indication D3, indication for inserting direction D4.

The assembling procedure (FIG. 13) includes the following acts: placing the strip 4, placing the draining piece 3, installing the lid 2. The assembled disc can achieve the uniform immunochromatographic reaction of 10 kinds of strips through some special designs. The stages 31 are arranged in axial symmetry, and fit with the fixing stoppers 32 and the fixing rivets 45 on the lid to make 10 strips arranging in axial symmetry with the sample pad gathering toward the symmetric axis. Therefore, with such spatial structure, the uniform immunochromatographic reaction on the various strips can be achieved. The excavate rivets 34 on the base fit with the salient rivets 46 on the lid to engage the disc, and two excavate rivets 34 disposed on the symmetric axis and four salient rivets 35 can also be used as fixing rivets 36 to fix the draining piece 3 and make it partly overlap the sample pad 103 of each strip. Consequently, with large bed volume and uniform internal structure, the draining piece 3 prevent the overflow of the liquid sample and ensure the even distribution of the sample to each strip, resulting in the uniform reaction on the different strips. The base 1 and the lid 2 of disc engage together to make the pressing pieces 42, 43, 44 on the inner side of the lid press on the overlapping areas of the absorbent pad 104 and the analytic membrane 101, the conjugate pad 102 and the analytic membrane 101, as well as the sample pad 103 and the conjugate pad 102, which ensures the continuity of immunochromatographic reaction inside the strips. The draining groove 41 on the inner side of the lid is comprised of integrated ten draining channels 40 corresponding to each strip. Each draining channel 40 includes two upper fringes 401 and one lower fringe 402. Every two draining channels 40 disposed on the same side of axis are linked by the connection board 403, while two draining channels 40 disposed on the different side of axis are linked by the connection board 404. The inner sides of two upper fringes are occluded with the edge of the stage 31 and extend directly to the underside of the base. The relationship between the height of the lower fringe h2 and that of the upper fringe h1 is as follows:

$$h2=h1-(\text{the height of the stage}+\text{the thickness of the sticky substrate of the strip}+\text{the thickness of the sample pad of strip}).$$

The relationship ensures that upper fringes 401 are occluded with the stage 31 and chuck to the underside of the base 1, and at the same time, the lower fringe 402 chucks to the sample pad 103 tightly. In addition, the face-axis end of stage 31 is sealed by the equal-height stopper 33. Therefore, following the engagement of the base and lid of disc, the stage 31, equal-height stoppers 33, the strips 4, the draining piece 3, the draining groove 41 and the underside of the base 1 and the inner side of the lid 2 define a whole closed sample pool and immunochromatographic channel, which can ensure that the sample can be distributed to each strip uniformly while preventing loss of the sample due to overflow. During the detection by the assembled disc, the liquid sample is dropped to the draining piece 3 through the sampling opening 47 and then the immune-reaction begins.

The process of the immunochromatographic reaction can be monitored through the endpoint indicating window 49 corresponding to the absorbent pad 103 during the detection and the final result can be read through the result observing window 48 corresponding to the analytic membrane. For the strips that can be analyzed quantitatively by the apparatus, the holding indication D3 and the indication for inserting direction D4 on the disc can indicate the inserting direction of the strip.

At last, a synchronous and uniform immunochromatographic reaction can occur on 10 kinds of strips by using the axially symmetric 10 strips-assembled disc. The final results can be shown visually.

What is claimed is:

1. An immunochromatographic strip disc for multiplexed detection, said strip disc being one of a circle, a square, a rectangle, a diamond, or a regular polygon, comprising:
    a base;
    a lid engaged with the base, wherein an inner side of such lid comprises a plurality of draining channels disposed thereon;
    a plurality of immunochromatic test strips disposed on the base, each test strip comprising a sample pad, an analytical membrane and a sticky substrate;
    a plurality of strip stages, disposed on the base, on which said test strips are carried, wherein said strip stages are arranged in a central or axial symmetry, the location and number of such strip stages corresponding to the location, number and position of each draining channel of the plurality of draining channels disposed on the lid, each test strip being fixed to the base via its sticky substrate;
    a sampling opening in the lid directly facing a draining piece and positioned at the geometric center of the lid, wherein said sampling opening intercommunicates to a draining groove provided on the inner side of the lid, said draining groove formed by the plurality of draining channels, wherein an edge of the draining piece laps to the sample pads adjacent to one end of the sampling opening; and
    wherein each draining channel comprises two upper fringes and a lower fringe, inner sides of the two upper fringes occlude with an edge of each strip stage and extend directly to the underside of the base, and wherein the lower fringe chucks tightly to the sample pad of the test strip, and wherein all draining channels are connected to one another sequentially.

2. The immunochromatographic disc of claim 1, wherein several sets of fixing stoppers are disposed along the edge of every test strip, and a numbering region is provided proximate each test strip near an edge of the base.

3. The immunochromatographic disc of claim 2, wherein each test strip comprises three protuberances with the end of each test strip adjacent to the symmetric center or axis is sealed by equal-height stoppers.

4. The immunochromatographic disc of claim 2, wherein several sets of pressing pieces are disposed at intervals on the inner side of the lid at the position where the channel of the draining groove extends outwards, and a result observing window, a endpoint indicating window and fixing rivets are sequentially disposed on the inner side of the lid.

5. The immunochromatographic disc of claim 4, wherein several rows of excavate rivets are disposed on the base, corresponding to salient rivets disposed on the inner side of the lid.

6. The immunochromatographic disc of claim 2, wherein numbers on the outer side of the lid correspond to those on the base; and a window used for marking a serial number of detected samples, a holding indication for users and an indication for inserting direction are disposed on the outer side of the lid.

7. The immunochromatographic disc of claim 1, wherein the height of the lower fringe, h2, is equal to a height of the upper fringes, h1, less the height of the test strip, which includes, the thickness of the sticky substrate and the thickness of the sample pad.

8. The immunochromatographic disc of claim 2, wherein the relationship between a height of the lower fringe h2 and a height of the upper fringes h1 is expressed as follows:

$$h2=h1-(\text{the height of the stage}+\text{the thickness of the sticky substrate of the strip}+\text{the thickness of the sample pad of the strip}).$$

9. The immunochromatographic disc of claim 3, wherein the relationship between a height of the lower fringe h2 and a height of the upper fringes h1 is expressed as follows:

$$h2=h1-(\text{the height of the stage}+\text{the thickness of the sticky substrate of the strip}+\text{the thickness of the sample pad of the strip}).$$

10. The immunochromatographic disc of claim 4, wherein the relationship between a height of the lower fringe h2 and a height of the upper fringes h1 is expressed as follows:

$$h2=h1-(\text{the height of the stage}+\text{the thickness of the sticky substrate of the strip}+\text{the thickness of the sample pad of the strip}).$$

11. The immunochromatographic disc of claim 5, wherein the relationship between a height of the lower fringe h2 and a height of the upper fringe h1 is expressed as follows:

$$h2=h1-(\text{the height of the stage}+\text{the thickness of the sticky substrate of the strip}+\text{the thickness of the sample pad of the strip}).$$

12. The immunochromatographic disc of claim 6, wherein the relationship between a height of the lower fringe h2 and a height of the upper fringe h1 is expressed as follows:

$$h2=h1-(\text{the height of the stage}+\text{the thickness of the sticky substrate of the strip}+\text{the thickness of the sample pad of the strip}).$$

13. A multiplexed immunochromatographic detection method used for qualitative detection by using the immunochromatographic disc according to claim 10, comprising the following acts:
1) assembling the immunochromatographic disc by placing different types of test strips on the corresponding strip stage with different numbers,
2) adding a liquid sample through the sampling opening and judge test endpoint through the endpoint indicating window,
3) observing and recording results of the different test strips through the result observing windows, and
4) comparing the test results with a standard so as to judge the occurrence of a certain kind of immunologic reaction and determine the existence of certain kinds of analytes.

14. A multiplexed immunochromatographic detection method used for quantitative detection by using the immunochromatographic disc according to claim 12, comprising the following acts:
1) assembling the immunochromatographic disc by placing different types of test strips on the corresponding strip stage with different numbers,
2) adding a liquid sample through the sampling opening and judge test endpoint through the endpoint indicating window,
3) according to the holding indication for users and the indication for inserting direction, inserting the disc into a detecting apparatus,
4) powering on the detecting apparatus to analyze one test strip quantitatively through the result observing window, a test result corresponding to the test strip being displayed on the apparatus,
5) rotating or moving the disc to the next strip and powering on the apparatus to perform another quantitative analysis,
6) repeating act 5) until all test strips on the disc are analyzed, and
7) determining the existence of a certain kind of analytes and its concentration.

* * * * *